United States Patent [19]

Bernstein

[11] 4,305,721

[45] * Dec. 15, 1981

[54] AGGLUTINATION ASSAY

[75] Inventor: David Bernstein, Sykesville, Md.

[73] Assignee: Becton Dickinson & Company, Paramus, N.J.

[*] Notice: The portion of the term of this patent subsequent to Dec. 15, 1998, has been disclaimed.

[21] Appl. No.: 137,585

[22] Filed: Apr. 7, 1980

Related U.S. Application Data

[63] Continuation-in-part of Ser. No. 68,165, Aug. 20, 1979.

[51] Int. Cl.³ .............................................. G01N 33/54
[52] U.S. Cl. .................................... 23/230 B; 23/915; 422/55; 422/61; 424/12
[58] Field of Search ................ 23/230 B, 915; 424/12; 422/55, 61

[56] References Cited

U.S. PATENT DOCUMENTS

| | | | |
|---|---|---|---|
| 3,424,558 | 1/1969 | Eldon | 23/915 X |
| 3,502,437 | 3/1970 | Mass | 23/230 B X |
| 3,853,468 | 12/1974 | Haymond | 23/915 X |
| 4,100,268 | 7/1978 | Scherr | 23/230 B X |

Primary Examiner—Arnold Turk
Attorney, Agent, or Firm—Louis E. Marn; Elliot M. Olstein

[57] ABSTRACT

An analyte is determined quantitatively by an agglutination assay by use of a method which includes the use of at least two analyte standards having different analyte concentrations; an analyte supported on a particulate support; specific binder for the analyte and buffered diluent for making serial dilutions of an analyte sample. The assay is preferably conducted on a test card which includes a sample portion and a standard portion, with the sample portion having a series of separated marked dilution areas for receiving dilutions of an analyte sample and the standard portion including separated marked standard areas for receiving analyte standard of different analyte concentration. By addition of binder and particles sensitized with analyte to the serial dilutions and standards, analyte can be determined quantitatively by multiplying the lowest standard concentration at which there is no visible agglutination by the highest reciprocal dilution of test sample which similarly shows no visible agglutination.

18 Claims, 1 Drawing Figure

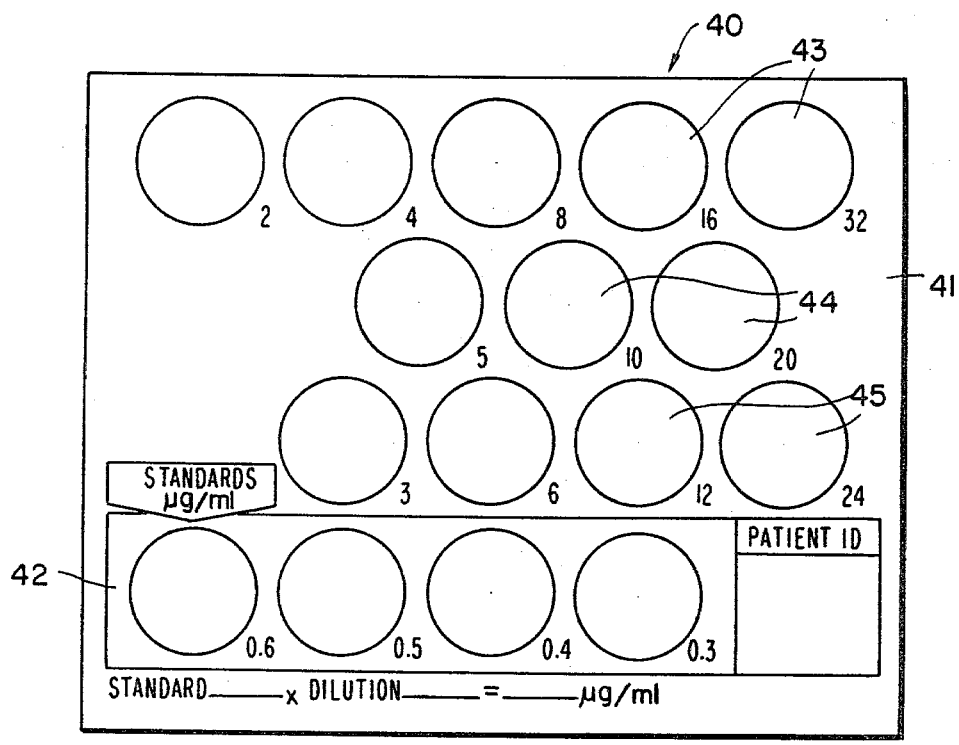

AGGLUTINATION ASSAY

This application is a continuation-in-part of U.S. application Ser. No. 068,165, filed on Aug. 20, 1979.

This invention relates to the assay of analytes, and more particularly to the assay of analytes by an agglutination assay. The term "analyte" as used herein, encompasses antigens, haptens, ligands which have naturally occuring binders, as well as antibodies and the naturally occurring binders.

Agglutination assays have been generally employed in the art for determining the presence of an analyte in a sample; however, in general, such agglutination assays have not been effective for making a quantitative determination of analyte in a sample. In addition, in general, such assays required an incubation period of at least one hour.

The present invention is directed to improving such agglutination assays by providing for a quantitative determination of an analyte, and in addition, the present invention is directed to providing for such quantitative determination in a shorter period of time.

In accordance with one aspect of the present invention, there is provided a test kit for the quantitative determination of an analyte in a sample by an agglutination procedure which includes at least two analyte standards having different analyte concentrations; analyte supported on a particulate support; specific binder for the analyte; and buffered diluent for making dilutions of an analyte sample.

In accordance with another aspect of the present invention, there is provided an article for use in the quantitative determination of an analyte in a sample which is a test substrate such as a card or plate, having a surface including a sample portion and a standard portion, with the sample portion including at least one series of separated marked dilution areas for receiving at least one series of dilutions of an analyte sample, and with the standard portion including at least two separated marked standard areas for receiving analyte standard of different analyte concentration, whereby quantitative determination of analyte in a sample can be conducted directly on the substrate by adding binder for the analyte and analyte sensitized particles to the dilution areas and the standard areas, and comparing inhibition of agglutination in the sample and standard areas.

In accordance with a further aspect of the present invention, there is provided an assay for the quantitative determination of an analyte in a sample by providing a series of dilutions of an analyte sample and at least two analyte standards, each having a different analyte concentration; adding binder for the analyte and particles sensitized with the analyte to each of the analyte standards and dilutions; and determining the lowest standard concentration and the highest reciprocal dilution (lowest concentration) of test sample which shows no visible agglutination. The quantity of analyte in the sample can then be determined by multiplying the concentration of such standard by the reciprocal of the dilution.

The present invention is applicable to assays for a wide variety of analyte for which an appropriate binder can be found, such as (1) antigens, which result in the formation of antibodies; when a vertebrate animal is immunized; (2) haptens, which when bound to a protein or a particulate carrier and introduced into a vertebrate, produce antibodies specific for the hapten, or (3) ligands which have naturally occurring binders which can be isolated in a form specific for the analyte. It is also to be understood that the analyte could be an antibody or a naturally occurring binder, in which case the binder for the analyte would be an antigen or an antibody to such antibody or naturally occurring binder.

As representative examples of analytes which can be assayed in accordance with the present invention, there may be mentioned:

(1) drugs, such as gentamicin; carbamazapine; phenytoin; valproic acid; salicylates; theophylline; barbituates; alkaloids, such as morphine, etc.

(2) amino acids, polypeptides, nucleotides, nucleosides and proteins, such as insulin, alphafetoprotein, complement components such as C1, C3, etc.;

(3) steroids, including; estrogens, androgens, adrenocortical hormones, bile acids, cardiotonic glycosides, aglycones as well as saponins. As specific examples, these may be mentioned; testosterone, androsterone, equilenin, estrone, estriol, progesterone, pregnenolone, 17-hydroxydioxy-corticosterone (compound S), deoxycorticosterone, cortisone, corticosterone cortisol, aldosterone, digoxin, digitoxin, etc.;

(4) vitamins, such as vitamin A, the B vitamin group, vitamin C, the D vitamins, and vitamins E and K; and (5) miscellaneous biological substances, such as, immunoglobulins, including IgG, IgA, and IgM; acute phase reactant proteins, such as CRP, $a_1$-acid glycoprotein, fibrinogen, $a_1$-antitrypsin, antitrombin III, serum transport proteins, such as, ceruloplasmin, haptoglobin, hemopexin, transferrin, etc. The term "analyte," as used herein, encompasses antigens, haptens, ligands which have naturally occurring binders, as well as antibodies and the naturally occurring binders.

The present invention has particular applicability to the assay of low molecular weight analytes (no greater than 1000) which are present in a test sample in an amount of at least $5 \times 10^{-7}$ moles/liter, although, in some cases, it may be possible to detect lower analyte concentrations. The sample which is assayed is generally a body fluid which contains or is suspected of containing the analyte.

The sensitized particle employed in the present invention is the analyte or appropriate analog thereof which is also bound by the binder employed in the assay, supported on a solid particulate support. The sensitized particles are of a type generally employed in the art, and the particulate support may be any one of a wide variety of materials which are employed in the art as a particulate support for a ligand. As representative examples of such materials, there may be mentioned: synthetic polymer supports, such as polystyrene, polypropylene, polyacrylates, polyamides, etc.; charcoal; lecithin/cholesterol particles; red blood cells; microbial cells; gelatin; and the like. A preferred support is polystyrene, somtimes referred to as a polystyrene latex. The selection of a suitable support is deemed to be well within the scope of those skilled in the art from the teachings herein.

The analyte may be supported on the particulate support by procedures known in the art. Thus, for example, the analyte may be supported on the support by adsorption or by covalent coupling. The analyte may be coupled or adsorbed to the support directly, or to the support coated with an appropriate coating material, such as a protein. The use of coupling agents for providing covalent binding between support and ligand is well known in the art, and no further details in this respect are deemed necessary for complete understanding of the present invention. Similarly, supporting of a ligand on a solid support by adsorption is also known in the art. The production of ligand or appropriate analog thereof on a solid particulate support forms no part of the present invention, and as a result, no further details in this respect are deemed necessary for complete understanding of the present invention.

The binder which is employed in the present invention is one which is specific for analyte to be assayed, as well as the supported analyte. Such binder can be a naturally occurring binder, but in general, the binder is an antibody which is specific to the antigen or hapten to be assayed. Such antibodies may be raised in an animal by procedures known in the art by either injecting the antigen or hapten coupled to a suitable antigenic carrier into a vertebrate to elicit appropriate antibody. The raising of antibody specific to a hapten is well known in the art, and as a result, no further details in this respect are deemed necessary for a complete understanding of the present invention.

In accordance with a preferred embodiment of the present invention, the antibody which is employed in the assay is one which has an avidity or affinity for the antigen or hapten to be assayed (analyte) such that there is a visible change between agglutination and nonagglutination upon a change in the analyte concentration in the standard of less than 33%, and preferably less than 20%. In order words, in the test, the difference in analyte concentration of two standards which effect a visible agglutination reaction and no visible agglutination should be 33% or less, and preferably 20% or less. Antibody having such affinity or avidity can be raised by immunizing the animal over a period of time sufficient to provide such avidity or affinity. Thus, the avidity or affinity of the antibody is increased by increasing the time over which the animal is immunized to raise the antibody, and such immunization is conducted over a period sufficient to provide an antibody having an affinity or avidity as hereinabove described.

As hereinabove indicated, the present invention provides a method in which there are provided analyte standards of at least two different concentrations, preferably three or four different concentrations in order to increase the accuracy of the assay. The specific standard concentrations will vary with the analyte to be assayed; however, such standard concentrations are selected by reference to the expected range of analyte concentration in the sample and the sample dilutions to be employed in the assay. By providing multiple standards of different concentrations, for each test, the standard concentrations at which there is a change from visible agglutination to no visible agglutination can be determined. In addition, by employing four standard concentrations, there can be obtained a control for both visible agglutination and no visible agglutination (agglutination inhibition).

The diluent which is employed in the assay method of the present invention is one which is suitable for the specific analyte to be assayed. Such buffers are well known in the art, and the selection of a suitable buffer is well within the scope of those skilled in the art from the teachings herein.

In accordance with the present invention, the assay is conducted by employing a series of dilutions of the analyte sample, and preferably at least three series of serial dilutions of the analyte sample. The number of serial dilutions in each sample, as well as the number of series of serial dilutions which is employed is dependent upon the desired accuracy of the assay, as well as the ability to provide an antibody having an affinity to provide a change between agglutination and non-agglutination with small changes in analyte concentration. The selection of a suitable number of serial dilutions and a suitable number of series of serial dilutions is deemed to be within the scope of those skilled in the art from the teachings herein.

Although the method of the present invention can be employed for an agglutination assay on any one of a wide variety of substrate surfaces, including slides, plates, and the like, the preferred embodiment of the method is the conducting of an assay on a card in accordance with the present invention.

The preferred embodiment will be further described with respect to the accompanying drawing, wherein:

The drawing is an embodiment of a card for use in an agglutination test.

It is to be understood, however, that the scope of the invention is not to be limited to the embodiment of the drawing.

Referring now to the drawing, there is shown a test card generally indicated as 40, which includes a sample portion, indicated as 41, and a standard portion, indicated as 42. The sample portion 41 includes three series of separated marked serial dilution areas for receiving three different series of serial dilutions of an analyte sample. The first series 43 includes five separated marked areas for providing serial analyte sample dilutions of 1:2, 1:4, 1:8, 1:16, and 1:32, designated as 2, 4, 8, 16 and 32, respectively. The second series 44 includes three separated marked serial dilution areas for providing serial dilutions of 1:5, 1:10 and 1:20, marked as 5, 10 and 20, respectively. The third series 45 includes four separated marked areas for providing serial dilutions of an analyte sample of 1:3, 1:6, 1:12, and 1:24, designated as 3, 6, 12 and 24, respectively.

The standard portion 42 of the card 40 includes four separated marked analyte standard areas for providing analyte standard at four different concentrations. As particularly shown, the marked standard areas are for analyte standards having concentrations of 0.6, 0.5, 0.4 and 0.3 $\mu g/ml$ of the analyte standard. The 0.6 concentration for the particular card shown is generally selected as a reagent control such that at such a concentration there is always no visible agglutination (100% inhibition), with the 0.3 concentration being selected as a reaction control so that there is always visible agglutination.

It is to be understood that the concentration selected for the standards will depend upon the analyte to be assayed, and are selected in a manner such that at least one of the standard concentrations provides visible agglutination and at least one of the standard concentrations provides no visible agglutination.

Similarly, the present invention is not limited to the dilution values particularly described in that the series and number of dilutions in each series will vary with the analyte to be assayed.

In employing the test card, the appropriate serial dilutions of the analyte sample are placed in the designated marked serial dilution areas. The appropriate standards are placed in the marked analyte standard areas. Subsequently, a fixed amount of antibody is dispensed onto all serial dilution sample areas and all standard areas on the card, followed by mixing and spreading to fill the entire area. The analyte sensitized particle in a fixed amount is then placed onto all serial dilution and standard areas, and the card is rotated first by hand, and then on a mechanical rotator. Immediately subsequent to the rotation, the standard circles are read to determine the lowest concentration of standard which shows no clumping; i.e., inhibition of agglutination. This is followed by determination of the test area with the highest dilution (lowest concentration) which shows no clumping; i.e., inhibition of agglutination.

The concentration of analyte in a test sample can then be calculated by multiplying the lowest standard concentration which shows 100% inhibition of agglutination, by the highest reciprocal dilution of test sample which shows 100% inhibition of agglutination. For example, if the 0.4 standard shows no clumping and test circle 20 shows no clumping, while circle 0.3 and circle 24 show clumping, then multiplying 0.4 times 20 gives a result of 8 micrograms per ml of analyte in the test sample.

As should be apparent, by using the test card, the dilution and the standards are provided on a single card for determining the concentration of analyte in a test sample. In addition, such a result can be achieved rapidly in that there is no necessity to await settling of appropriate pellets. Furthermore, by providing different standard concentrations and several series of serial dilutions, there can be obtained a quantitative accuracy for determining concentration of analyte in the sample.

The invention will be further described with respect to an embodiment thereof in the following example. The example is directed to an inhibition of agglutination assay for gentamicin; however, it is to be understood that the teachings with respect to the gentamicin assay are equally applicable for an assay for other analytes.

EXAMPLE 1

Preparation of Rabbit anti gentamicin antisera

Gentamicin covalently coupled to bovine serum albumin (BSA) by use of 1-ethyl 3- (dimethyl aminopropyl) carbo-diimide hydrochloride (ECDI) (0.9 mole gentamicin per mole BSA) is diluted in 0.05 M phosphate buffer solution, pH 7.2, to a final protein concentration of 2.0 mg/ml and emulsified with an equal volume of complete Freund's adjuvant. One milliliter of the emulsion was injected intramuscularly into the rear flank of each of ten New Zealand albino rabbits. Rabbits were injected Day 1, 15 and boosted once per month and test bled from the medial ear artery. Antisera was diluted and reacted with gentamicin latex antigen suspension. When a satisfactory antibody titer was attained, rabbits were bled weekly. The antisera were sterile filtered, sodium azide was added to a final concentration of 0.1% and then stored at 4° C.

EXAMPLE 2

Preparation of Gentamicin Orosomucoid Conjugate

Orosomucoid was purified from Bovine serum fraction VI glycoprotein (ICN) utilizing carboxymehtyl cellulose column. The first eluted peak on 0.025 M acetate buffer pH 4.0 was diluted to a final protein concentration of 6 mg/ml $E_{1\%}^{280} = 8.9$ in acetate buffer. In a typical experiment 16.0 mg of orosomucoid was mixed with 300 mg of gentamicin. 750 mg of ECDI was added in 2.5 ml of acetate buffer pH 4.0. The reaction mixture was incubated for 18 hours at 4° C. and then extensively dialyzed against distilled water.

EXAMPLE 3

Preparation of Gentamicin Orosomucoid Sensitized Particles

Polystyrene latex (0.945 $\mu$ 10%, Dow Diagnostics) was washed three times with 10 volumes of 0.02 M glycine buffer pH 8.6. The latex was adjusted to a final concentration of 1% latex. Gentamicin orosomucoid conjugate was diluted in distilled water to a final concentration having an optical density at 280 nm of 0.110. 5.0 ml of 1% washed latex was added to each of 5 corex glass tubes. The gentamicin orosomucoid conjugate was added in 0.100 ml increments from 0.300 ml to 0.700 ml to each tube containing latex. The tubes were vortexed and incubated for one hour at 37° C. 1.0 ml of 0.2% ovalbumin. 0.02 M glycine buffer pH 8.6 was added to each tube and the tubes were incubated for an additional 15 minutes at 37° C. The tubes were centrifuged at 2000 g, supernatant decanted and the particles resuspended in 4.0 ml of 0.02 M glycine buffer pH 8.6. 1.0 ml of 2.5% glutaraldehyde was added to each tube in order to crosslink the adsorbed protein for stability. The tubes were incubated for one hour at 37° C. The The tubes were each centrifuged and washed two times with 10.0 ml of 0.02 M glycine buffer pH 8.6. The latex pellets were each resuspended in 5.0 ml of resuspending buffer containing 0.05% polysorbate 80, 0.5% ovalbumin, 0.1 M glycine buffer pH 8.6, 0.17 NaCl, and 0.1% sodium azide. The latex conjugates were then heated for two hours at 56° C., cooled to room temperature, and then assayed.

EXAMPLE 4

Reagents

1. Sensitized gentamicin particle suspension
   1.0% of the sensitized particles prepared in Example 3, 0.05% polysorbate 80, 0.1 M glycine buffer, pH 8.2, 0.17 M sodium chloride, 0.2% sodium azide (preservative), and 0.5% ovalbumin.
2. Gentamicin Standards containing 0.6, 0.5, 0.4 and 0.3 micrograms ($\mu$g) gentamicin per milliliter (ml), 0.05 M phosphate buffered saline, pH 7.4, 0.1% sodium azide (preservative), and 10% human serum.
3. Gentamicin Antibody from Example 1 diluted in 50% human serum and 0.05 M phosphate buffered saline, pH 7.4, to obtain appropriate reactivity with gentamicin sensitized particles and gentamicin standards, 0.1% sodium azide (preservative).
4. Buffered Diluent contains 0.05 M phosphate buffered saline, pH 7.4 containing 0.1% sodium azide (preservative) and 20% human serum.

PROCEDURE

Place 25 microliters of buffered diluent onto the circles designated 2, 4, 8, 16, 32, 10, 20, 6, 12 and 24 of the card of the drawing, followed by placing of 100 microliters onto circle 5 and 50 microliters onto circle 3.

25 microliters of a serum sample is added to the buffered diluent in circle 2 and thoroughly mixed. 25 microliters of the diluted sample of circle 2 is transferred to circle 4 and mixed. Employing the same procedure, the serial dilution is completed in the first horizontal row of the card; namely, circles 8, 16 and 32, with 25 microliters being drawn up and discarded from the last circle of the row. Each circle now contains a dilution of test sample, the reciprocal of which is the number found at the lower right of each test circle.

25 microliters of serum sample is dispensed onto circle 5 of the card and mixed. Serial dilution is then completed for the next two circles; namely, circles 10 and 20, employing the hereinabove described procedure. 75 microliters from circle 5 is then discarded, by discarding three 25 microliter aliquots.

25 microliters of serum sample is dispensed onto circle 3. The sample is then serial diluted to the remaining horizontal circles in the row; namely, circles 6, 12, 24, by the procedure hereinabove described. 25 microliters is then discarded from circle 3.

As a result of the above procedure there are now 25 microliters of a 1:2, 1:4, 1:8, 1:16, 1:32, 1:5, 1:10, 1:20, 1:3, 1:6, 1:12 and 1:24 dilution of serum sample in circles 2, 4, 8, 16, 32, 5, 10, 20, 3, 6, 12 and 24, respectively.

25 microliters of 0.6 micrograms gentamicin per ml standard is applied to the first standard circle (designated 0.6) on the card. The procedure is then repeated for the remaining standard circles marked 0.5, 0.4 and 0.3, employing the corresponding gentamicin standard.

25 microliters of antibody is then dispensed onto all test and standard circles on the card, followed by mixing and spreading the reactants on each of the sample circles to thereby fill the entire circle. This is then followed by mixing and spreading of all standard circles.

The sensitized gentamicin particle suspension is then placed onto all test and standard circles in an amount of approximately 1/60 ml. The card is then rotated three or four times back and forth by hand, followed by placing the card on a mechanical rotator and rotation for 8 minutes under a moistened humidifier. Immediately subsequent to mechanical rotation, the card is then hand rotated using three or four back and forth motions. Under a high intensity lamp, the standard circles from 0.3 to 0.6 is read to determine the lowest concentration of standard which shows no clumping; i.e., inhibition of agglutination. This is followed by determination of the test circle with the highest dilution (lowest concentration) which shows no clumping; ie., inhibition of agglutination.

The test results can be recorded directly on the card, and the concentration of gentamicin in the test sample can be calculated by multiplying the lowest standard concentration which shows no clumping (100% inhibition), by the highest reciprocal dilution of test specimen which shows no clumping (100% inhibition). For example, if the 0.5 microgram/ml standard shows no clumping and circle 16 shows no clumping, while circle 0.4 micrograms per ml and circle 20 shows clumping, then multiplying 0.5 times 16 gives a result of 8 micrograms per ml. gentamicin in the test specimen.

The standard circles marked 0.3 and 0.6 serve as reagent controls. The circle marked 0.3 is a reactive control and should show definite clumping. Circle 0.6 is a nonreactive control and should show no clumping.

Numerous modifications and variations of the present invention are possible in light of the above teachings and, therefore, within the scope of the appended claims, the inventio may be practiced otherwise than as particularly described.

I claim:

1. An article for use in the quantitative determination of an analyte by inhibition of agglutination, comprising: a test card, said test card having a surface including a sample portion and a standard portion said sample portion being comprised of at least one series of separated marked serial dilution areas for receiving at least one series of serial dilutions of an analyte sample each having an indicia of the dilution, said standard portion including at least two separated marked standard areas for receiving analyte standard of different analyte concentration each having an indicia of the analyte concentration, whereby a quantitative determination of analyte in a sample can be determined directly on the test card by serial dilution of sample on the test substrate, adding a binder for the analyte and analyte sensitized particles to the serial diluted analyte samples and analyte standards and determining the lowest standard concentration and the highest dilution at which agglutination is inhibited.

2. The article of claim 1 wherein the sample portion includes at least three series of separated marked dilution areas for receiving three series of serial dilutions.

3. The article of claim 2 wherein the standard portion includes four separated marked standard areas for analyte standards of different analyte concentration.

4. A test kit for quantitative determination of an analyte in a sample by inhibition of agglutination, comprising:

at least two analyte standards having different analyte concentrations; analyte sensitized particles; a binder for the analyte; buffered diluent for making serial dilutions of an analyte sample; and a test card, said test card having a surface including a sample portion and a standard portion, said sample portion being comprised of at least one series of separated marked serial dilution areas for receiving a series of serial dilutions of an analyte sample each having an indicia of the dilution, said standard portion including at least two separated marked standard areas for receiving analyte standards of different analyte concentration, each having an indicia of the analyte concentration, whereby a quantitative determination of analyte in a sample can be determined directly on the test card by serial dilution of sample on the test substrate, adding the binder for the analyte and analyte sensitized particles to the serial diluted analyte samples and analyte standards and determining the lowest standard concentration and the highest dilution at which agglutination is inhibited.

5. The kit of claim 4 wherein the binder is an antibody.

6. The kit of claim 5 wherein the antibody has an avidity for the analyte whereby there is a visible change between agglutination and nonagglutination upon a change in analyte concentration in the standard of less than 33%.

7. The kit of claim 6 wherein the antibody has an avidity whereby there is a visible change between agglutination and non-agglutination with a change in analyte concentration in the standard of 20% or less.

8. The kit of claim 6 wherein the analyte is a drug.

9. The kit of claim 6 wherein the analyte is a hapten.

10. The kit of claim 6 wherein the sample portion includes at least three series of separated marked dilution areas for receiving three series of serial dilutions.

11. The kit of claim 10 wherein the standard portion includes four separated marked standard areas for analyte standards of different analyte concentration and wherein there are at least four analyte standards of different analyte concentration, one standard providing a control for visible agglutination and one standard providing a control for no visible agglutination.

12. An assay for quantitative determination of an analyte comprising:

serial diluting an analyte sample directly on at least one series of separated marked serial dilution areas on a surface of a test card, each of the dilution areas having an indicia of the dilution; providing at least two analyte standards, each having a different analyte concentration on separated marked standard areas on a surface of the test card, each of the standard areas having an indicia of the analyte concentration; adding binder for the analyte and particles sensitized with analyte to each of the analyte standards and each of the analyte sample serial dilutions; and determining the quantity of analyte in the sample from the lowest standard concentration and the highest reciprocal sample dilution which shows no visible agglutination.

13. The assay of claim 12 wherein the analyte is a drug.

14. The assay of claim 12 wherein the analyte is a hapten.

15. The assay of claim 12 wherein the binder is an antibody.

16. The assay of claim 15 wherein the antibody has an avidity for the analyte whereby there is a visible change between agglutination and nonagglutination upon a change in analyte concentration in the standard of less than 33%.

17. The assay of claim 16 wherein there are at least four analyte standards of different analyte concentration, one standard providing a control for visible agglutination and one standard providing a control for no visible agglutination.

18. The assay of claim 17 wherein the assay is effected with at least two different series of serial dilutions of the sample.

* * * * *